United States Patent
Devlin et al.

(10) Patent No.: US 6,654,626 B2
(45) Date of Patent: Nov. 25, 2003

(54) ELECTRODE ARRAY SYSTEM FOR MEASURING ELECTROPHYSIOLOGICAL SIGNALS

(75) Inventors: Philip H. Devlin, Brookline, MA (US); Rafael M. Cordero, Tewksbury, MA (US); Nassib G. Chamoun, W. Roxbury, MA (US); John R. Shambroom, Arlington, MA (US); Charles Fendrock, Sudbury, MA (US); Terrie L. McDaniel, San Antonio, TX (US)

(73) Assignee: Aspect Medical Systems, Inc., Newton, MA (US)

( * ) Notice: Subject to any disclaimer, the term of this patent is extended or adjusted under 35 U.S.C. 154(b) by 0 days.

(21) Appl. No.: 10/156,305

(22) Filed: May 28, 2002

(65) Prior Publication Data

US 2002/0183605 A1 Dec. 5, 2002

Related U.S. Application Data

(62) Division of application No. 09/513,760, filed on Feb. 25, 2000, now Pat. No. 6,394,953, which is a division of application No. 08/730,638, filed on Oct. 11, 1996, now Pat. No. 6,032,064.

(51) Int. Cl.[7] .......................................... A61B 5/0478
(52) U.S. Cl. .................. 600/383; 600/372; 600/391; 600/393; 600/396; 600/397; 607/152; 607/153
(58) Field of Search .......................... 600/382, 383, 600/384, 385, 391–393, 372, 386, 397; 602/149, 152, 153

(56) References Cited

U.S. PATENT DOCUMENTS

| | | | |
|---|---|---|---|
| 3,490,439 A | 1/1970 | Rolston | 128/2.1 |
| 3,762,396 A | 10/1973 | Ballantine et al. | 600/26 |
| 3,774,592 A * | 11/1973 | Lahr | 600/392 |
| 3,774,593 A | 11/1973 | Hakata et al. | 600/544 |
| 3,888,240 A * | 6/1975 | Reinhold et al. | 600/390 |
| 3,946,723 A | 3/1976 | Servos | 600/546 |
| 3,999,826 A | 12/1976 | Yurtin | 399/17 F |
| 4,033,333 A * | 7/1977 | DeSalvo et al. | 600/393 |
| 4,072,145 A * | 2/1978 | Silva | 600/383 |
| 4,082,087 A * | 4/1978 | Howson | 600/391 |
| 4,122,843 A * | 10/1978 | Zdrojkowski | 600/382 |
| 4,353,372 A * | 10/1982 | Ayer | 600/393 |
| 4,474,186 A | 10/1984 | Ledley et al. | 600/546 |
| 4,495,950 A * | 1/1985 | Schneider | 600/483 |
| 4,537,198 A | 8/1985 | Corbett | 600/383 |
| 4,580,557 A | 4/1986 | Hertzmann | 606/12 |
| 4,595,013 A * | 6/1986 | Jones et al. | 600/383 |
| 4,638,807 A * | 1/1987 | Ryder | 600/383 |
| 4,640,290 A | 2/1987 | Sherwin | 128/642 |
| 4,683,892 A | 8/1987 | Johansson et al. | 128/639 |
| 4,706,679 A * | 11/1987 | Schmidt et al. | 600/383 |
| 4,709,702 A | 12/1987 | Sherwin | 128/639 |

(List continued on next page.)

FOREIGN PATENT DOCUMENTS

| | | |
|---|---|---|
| EP | 0 381 480 | 8/1990 |
| EP | 0 452 834 | 10/1991 |
| EP | 0 686 407 | 12/1995 |
| GB | 2 075 194 | 11/1981 |
| WO | 96/11631 | 4/1996 |

*Primary Examiner*—Lee Cohen
(74) *Attorney, Agent, or Firm*—Hale and Dorr LLP

(57) ABSTRACT

An array of electrodes is constructed to allow the user to easily adjust to the correct size of the patient's head. The array is self-adhesive, pre-gelled and disposable. The array fits easily over the temple and forehead areas where EEG signals can be acquired by specially designed monitors for purposes of monitoring a number of bodily phenomena, including but not limited to, depth of anesthesia, and/or ischemia, and burst suppression. The array is connected to the monitor via a tab connector that is integral to the disposable device. The tab connector is insertible into a reusable connector that is part of a monitoring system.

12 Claims, 14 Drawing Sheets

U.S. PATENT DOCUMENTS

| | | | |
|---|---|---|---|
| 4,770,180 A | 9/1988 | Schmidt et al. | 128/644 |
| 4,928,696 A | 5/1990 | Henderson et al. | 128/644 |
| 4,936,306 A | 6/1990 | Doty | 128/642 |
| 4,967,038 A | 10/1990 | Doty | 128/642 |
| 5,042,481 A * | 8/1991 | Suzuki et al. | 600/393 |
| 5,265,579 A * | 11/1993 | Ferrari | 600/385 |
| 5,305,746 A * | 4/1994 | Fendrock | 600/391 |
| 5,327,888 A * | 7/1994 | Imran | 600/393 |
| 5,341,806 A * | 8/1994 | Gadsby et al. | 600/393 |
| 5,495,853 A | 3/1996 | Yasushi | |
| 5,660,177 A * | 8/1997 | Faupel et al. | 600/382 |
| 5,701,894 A | 12/1997 | Cherry et al. | |
| 5,772,591 A * | 6/1998 | Cram | 600/383 |
| 5,813,404 A | 9/1998 | Devlin et al. | |

* cited by examiner

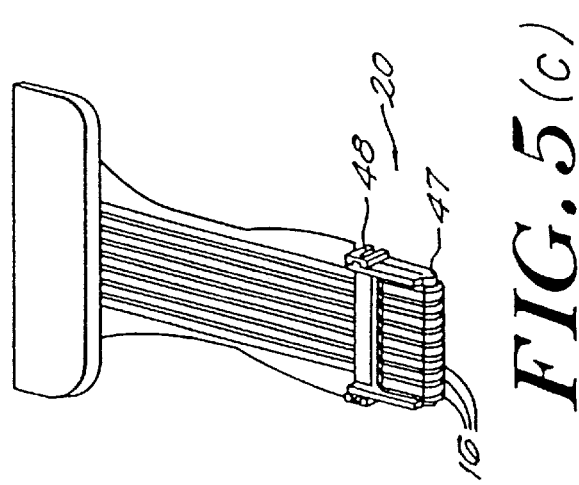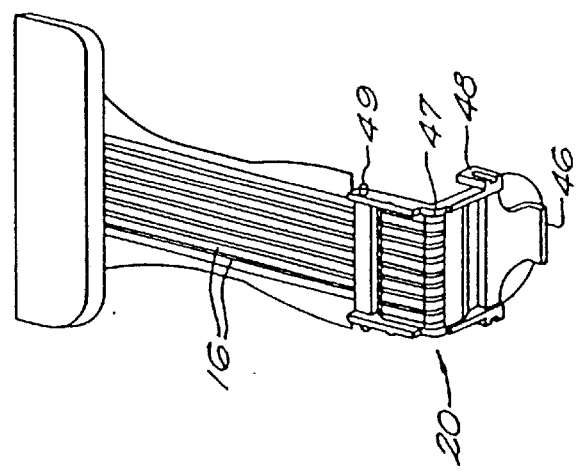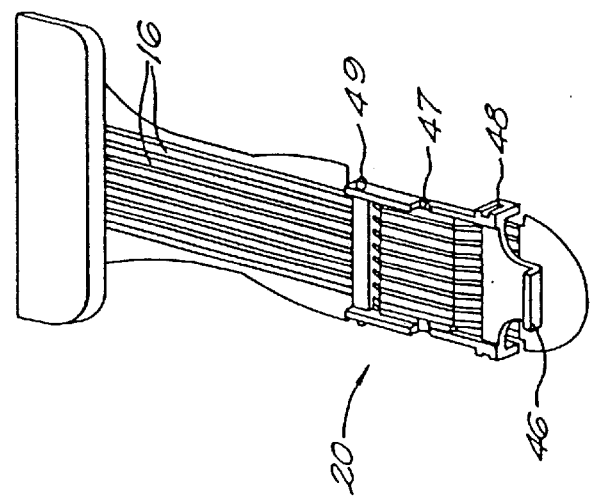

ELECTRODE ARRAY SYSTEM FOR MEASURING ELECTROPHYSIOLOGICAL SIGNALS

CROSS REFERENCE TO RELATED APPLICATIONS

This application is a divisional of U.S. patent application Ser. No. 09/513,760, filed on Feb. 25, 2000, (now U.S. Pat. No. 6,394,953) which is a divisional of U.S. patent application Ser. No. 08/730,638, filed on Oct. 11, 1996, (now U.S. Pat. No. 6,032,064).

BACKGROUND OF THE INVENTION

This invention relates to physiological electrical signal monitors and more particularly to a self-prepping multiple electrode array to connect to such monitors.

Surgical procedures are becoming more non-invasive, and as a result the use of non-invasive electrophysiological monitoring to evaluate global changes of a patient's condition during surgical procedures has increased significantly. For example, EEG monitors are now being used for monitoring cerebral function during intra-operative procedures. Of particular interest are the assessment of the effects, of anesthetics, the evaluation of asymmetric activity between the left and right hemispheres of the brain in order to detect cerebral ischemia, and the detection of burst suppression.

One of the greatest impediments to making intra-operative EEG monitoring more widely practiced in the medical community is the traditional use of multiple electrodes in the standard International (10–20) Electrode Placement on the head, primarily in the scalp. Applying them takes considerable time and expertise, requires multiple, separate and time consuming skin preparation steps, and leaves the patient's scalp and hair in disarray.

Various headsets and caps are studded with different style electrodes to speed this process, but such headsets and caps are generally not disposable (and therefore must be cleaned), need to be adjusted to accommodate the widely varying dimensions of the patients' heads, and require a considerable up-front cost. Other problems are encountered in the present medical environment when such headsets and caps are designed to be single-use disposable devices because such devices are on occasion re-used despite warnings, which results in the spread of infection. Such headsets and caps have also been used with equipment for which it was not designed, which may be a well intentioned cost saving practice, but which could result in degraded performance of the device.

The most widely used electrodes are the reusable "gold cup" style electrodes that are small, bare tin, silver, or gold plated metal cups on the end of unshielded wires that may be several feet long. Such electrodes may require that the multiple scalp and forehead electrode sites first be located by measuring and marking the head. Such sites must then be prepared before applying the electrode in order to get good electrical contact. This preparation is usually accomplished by abrading the electrode sites with a grit-impregnated solution or with some other abrasive means to remove the outer layers of skin which cause the poor electrical contact. The electrodes, up to 19 on the scalp for the full International (10–20) electrode placement, are then individually applied with adhesive to the prepared sites in contact with a blood-enriched skin layer, and are then injected with conductive electrolyte cream through the hole in the top of the electrode, thereby providing a relatively low electrical contact impedance. This process leaves the patient with abraded spots, adhesive, and electrolyte cream throughout the scalp. Frequently, contact between the metal electrode and the skin occurs, causing a time-varying offset voltage that results in "baseline wander." The electrodes also need to be placed with reasonable accuracy to achieve the standard placements or montages and to be able to repeat the same measurement at a later time.

The need to use multiple, separate preparation steps makes the set-up a very time consuming process, taking perhaps up to half an hour of a medical technician's time for even a small subset of the full International (10–20) Electrode Placement. The amount of expertise and time required to prepare a patient is presently an impediment to intraoperative EEG monitoring being more widely practiced. Also, care is needed to bundle the unshielded leads to reduce electrical noise interference. Additionally, after the procedure is over, the gold cup electrodes and any placement harness need to be cleaned and sterilized since they are not intended to be disposable.

A number of prior art multiple electrode assemblies have been developed for EEG monitoring. U.S. Pat. No. 4,595,013 issued to Jones; U.S. Pat. No. 4,928,696 issued to Henderson; U.S. Pat. No. 4,638,807 issued to Ryder; U.S. Pat. No. 4,072,145 issued to Silva; and U.S. Pat. No. 3,490,439 issued to Rolston are several examples. These multiple electrode assemblies, however, all require some or all of the multiple, separate and time consuming steps of skin preparation described above to reduce the contact impedance with the skin before they are applied to the body. These separate skin preparation steps also make it difficult to improve contact impedance once the electrode has been applied to the patient or after the medical procedure is underway. If the preparation was inadequate at the time the multiple electrode assembly is applied, it must be removed, the skin reabraded, and most likely a new electrode assembly would have to be reapplied, adding additional expense to the additional preparation time. Too much abrasion can cause a skin injury, or bleeding, leaving the patient with a lasting wound. Separate devices required to abrade the skin cause the risk to the applicator by potential contact with blood and by possible disease transmittal during preparation.

There are also a number of prior art multiple electrode assemblies that are self prepping. U.S. Pat. No. 4,709,702 and associated electrode U.S. Pat. No. 4,640,290, both issued to Sherwin, utilize an array of spring loaded metal "tulip" electrodes in a reusable headset that penetrates the outer dead layers of skin to achieve a low contact impedance. Also, U.S. Pat. No. 4,770,180 and associated electrode U.S. Pat. No. 4,706,679 both issued to Schmidt utilize an array of stiff, bundled metal wires that contact and penetrate the patient's skin. The drawback with both of these assemblies is that the metal contact with the skin causes highly undesirable time-varying offset voltages that interfere with the sensitive measurement of the small signal voltages of the body. Also, both of these assemblies, and other assemblies that utilize a headset or cap such as the assembly described in U.S. Pat. No. 4,967,038 issued to Gevins, need some adjustment to properly position the electrodes on the widely varying dimensions of the patients' heads, and require a high up-front cost and cleaning after use.

U.S. Pat. No. 4,936,306 issued to Doty utilizes a spiral coil electrode that may be metallic, and that uses corkscrews into patient's skin to achieve low contact impedance. While this may achieve low contact impedance, it has the significant drawbacks of discomfort to the patient and creating sites of possible infection because of the deep skin punctures made by the spiral coils. If made of metal, the spiral coils will also cause time-varying voltages. Lastly, these electrodes are actually applied individually since they must be screwed into the patient's scalp, which adds time to the procedure.

U.S. Pat. No. 4,683,892 issued to Johansson utilizes a headset with multiple electrodes that are activated by compressed air, which impinge against the patient's scalp, and that also dispense electrolyte paste to improve contact. This is a complex and expensive device, not intended for general, routine use in an intraoperative environment.

It is therefore a principal object of the present invention to provide a disposable, pre-gelled, self-prepping multiple electrode array which easily and reliably prepares the skin to assume a relatively low contact impedance.

Another object of the present invention is to provide a self-prepping multiple electrode array that does not require the use of more than one component to be handled by the person applying the device, and fits most head sizes in the general patient population.

Still another object of the present invention is to provide a multiple electrode array that can monitor cerebral function without the use of electrodes placed in the scalp, and that is easily aligned on the head.

A further object of the present invention is to provide a multiple electrode array that prevents its use with monitoring equipment with which it was not intended to be used.

SUMMARY OF THE INVENTION

An array of electrodes is constructed to allow the user to easily adjust to the correct size of the patient's head. The array is self-adhesive, pre-gelled and disposable. The array fits easily over the temple and forehead areas where EEG signals can be acquired by specially designed monitors for purposes of monitoring a number of bodily phenomena, including but not limited to, depth of anesthesia, and/or ischemia, and burst suppression. The array is connected to the monitor via a tab connector that is integral to the disposable device. The tab connector is insertible into a reusable connector that is part of a monitoring system.

The reusable connector is made of rigid contacts positioned side by side within a keyed cavity. The contacts press against conductors of the disposable array when the conductors are inserted into the cavity of the reusable connector. The conductors of the disposable array are laid on a flexible circuit constructed of a polyester substrate that has a plastic clip as its backing and support. The flexible circuit when routed through this clip forms the tab connector. This sensor tab connector, when inserted into the reusable connector cavity, electrically connects the electrodes to the monitor, allowing the acquisition of the electrophysiological signals. The clip of the tab connector is self securing, and thus does not need any additional securing mechanism to keep the flexible circuit in place. The reusable connector and the disposable connector have complementary locking mechanisms that provide for a secure connection.

Depending on the application and uniqueness of the array, a tab connector may be used which includes a key that only fits to specific monitors. The array also can communicate with the monitor to indicate the type of application utilizing the electrodes and how many channels need to be configured.

The array contains two or more elements that when pressed against the skin lower their contact impedance to the skin and thus provide better quality signals. The elements contain built in blowout pockets that allow for the gel to adjust itself when pressure is applied to it. Such pockets also prevent the gel from getting blown into the adhesive areas or running into other element areas, which could cause channels to short circuit.

These and other objects and features of the present invention will be more fully understood from the following detailed description which should be read in conjunction with the accompanying drawings in which correspondence reference numerals refer to corresponding parts throughout the several views.

BRIEF DESCRIPTION OF THE DRAWINGS

FIGS. 5(a) through 5(c) are perspective views of a tab clip assembly utilized by the electrode array shown in FIG. 1 with a substrate is routed through it;

DETAILED DESCRIPTION OF THE PREFERRED EMBODIMENTS

Figure 1:
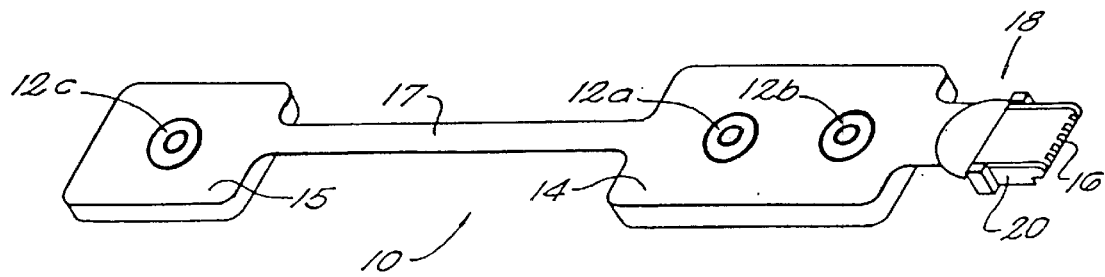
FIG. 1 is a perspective view of the preferred embodiment of the electrode array of the present invention.
Figure 2:
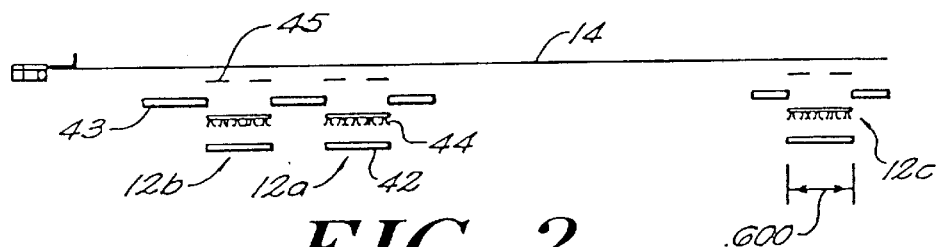
FIG. 2 is a side sectional view of the electrode array shown in FIG. 3 taken along lines 2—2 of FIG. 3.

Referring to FIGS. 1–4, an electrode array 10 is shown. In a preferred embodiment the array 10 includes three electrodes 12 that are self adherent and self prepping to the forehead and temple areas and that are used to acquire electrophysiological (EEG) signals. This array 10 comprises a flexible circuit 14 containing silver/silver-chloride (Ag/AgCl) conductors 16 on a polyester substrate. These conductors are routed from specific montage locations to a single connecting tab 18. There can be up to eight (8) conductors 16 for providing up to eight signal lines of EEG data which can be captured simultaneously. This tab 18 contains a clip 20 which adds rigidity, a locking mechanism, self alignment, polarity and a keying mechanism to the array. The clip 20 also adds a solid contact area to the flexible circuit 14.

The array 10 comprises a main body 14 which in the embodiment shown includes two electrodes 12a, 12b and a satellite body 15 which includes one electrode 12c. The satellite body 15 allows the monitoring personnel to adjust the placement of the electrode 12c mounted on the satellite body 15 due to the patient's head size. Extension 17, through which conductors 16 run, connects the main body 14 to the satellite body 15.

Figure 3:
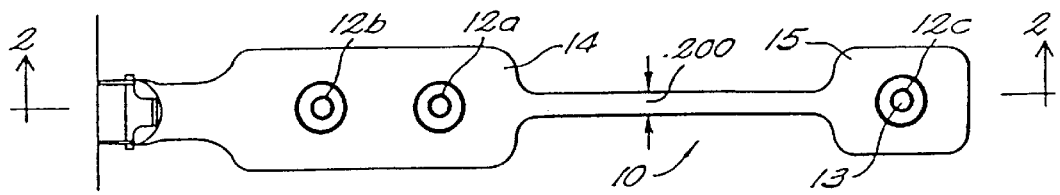
FIG. 3 is a top plan view of the electrode array shown in FIG. 1.
Figure 14:
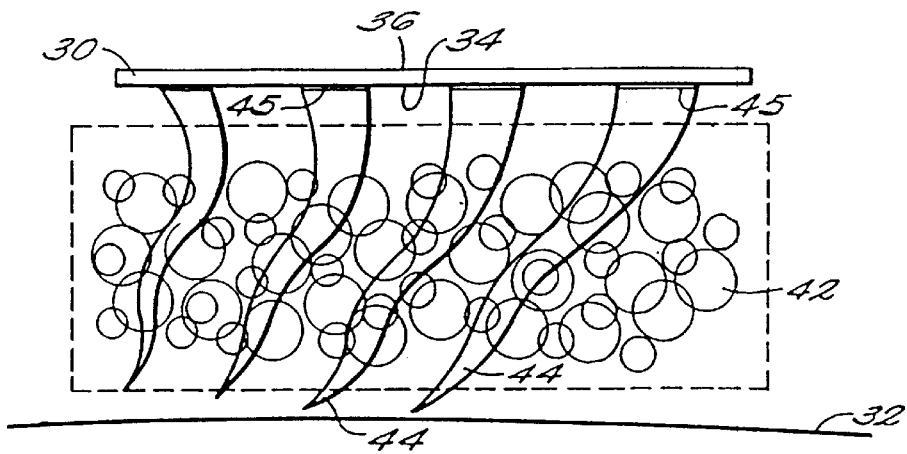
FIG. 14 is an elevational view showing the sponge over tines construction of the electrodes of the present invention.

Referring to FIGS. 3 and 14, each of the three electrodes 12 mounted in the array 10 contain a self prepping disk 30 which includes a set of flexible tines 44 mounted with adhesive 45. The flexible tines 44 extended beyond the surface of the gel 40 to contact the skin 32 as part of the normal application of the electrode 12 to the skin 32. When pressure is applied to the electrodes 12, the flexible tines 44 are pushed through foam layer 42 against the skin 32, which causes the tines 44 to part the high impedance outer layers of skin 32 to expose the low impedance, blood-enriched layers without scratching or abrading. This prepping disk is made out of a plastic such as nylon constructed as hooks from hook and loop fasteners of the type often said under the Velcro trademark. These hooks are then sheared to the correct height and stiffness. The electrodes 12 are surrounded by an adhesive backed foam layer 43. The array contains markers 13 that indicate the correct locations that need to be pressed to achieve the desired skin impedance.

Figure 4:
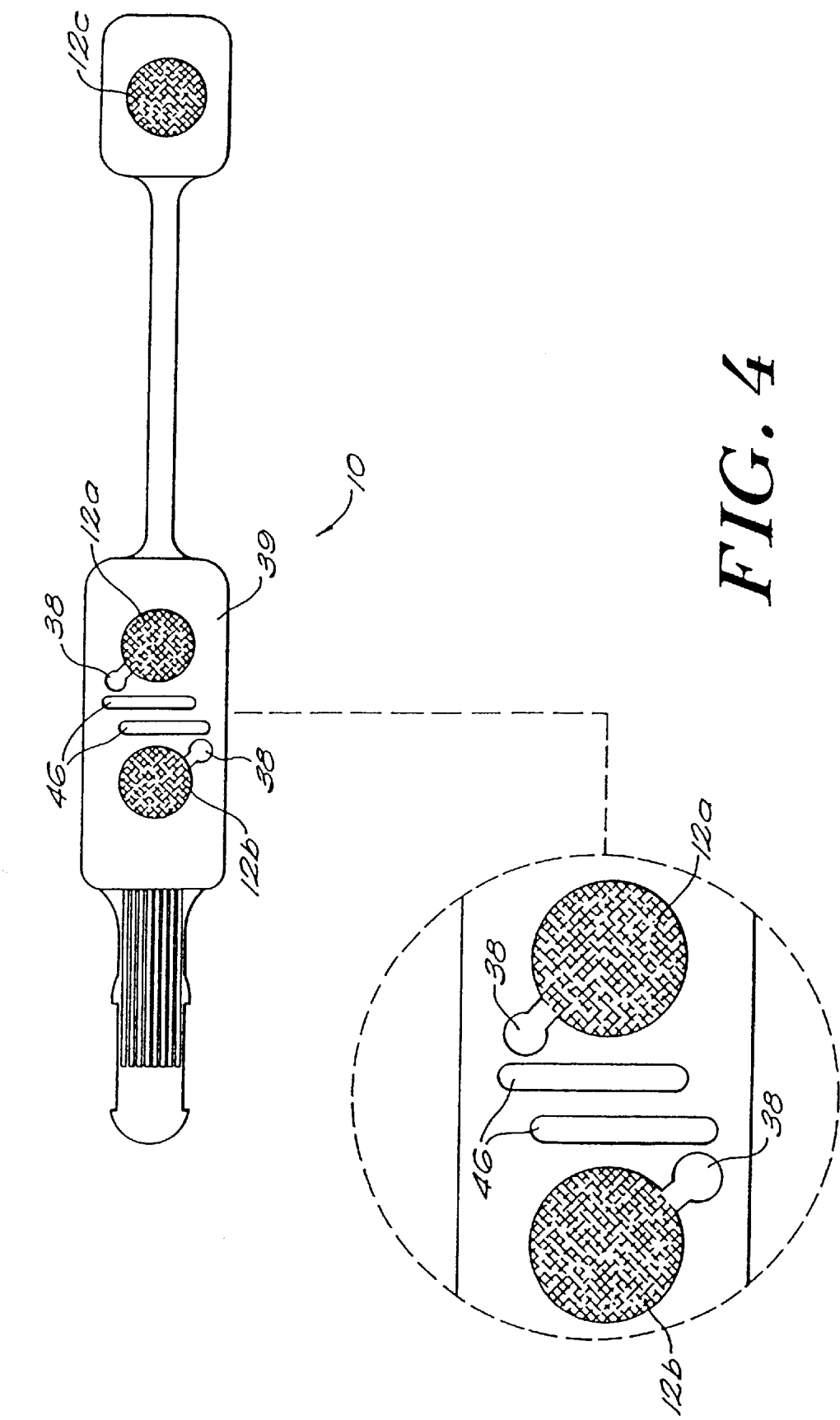
FIG. 4 is a bottom sectional view of the electrode array shown in FIG. 2.
Figure 12:
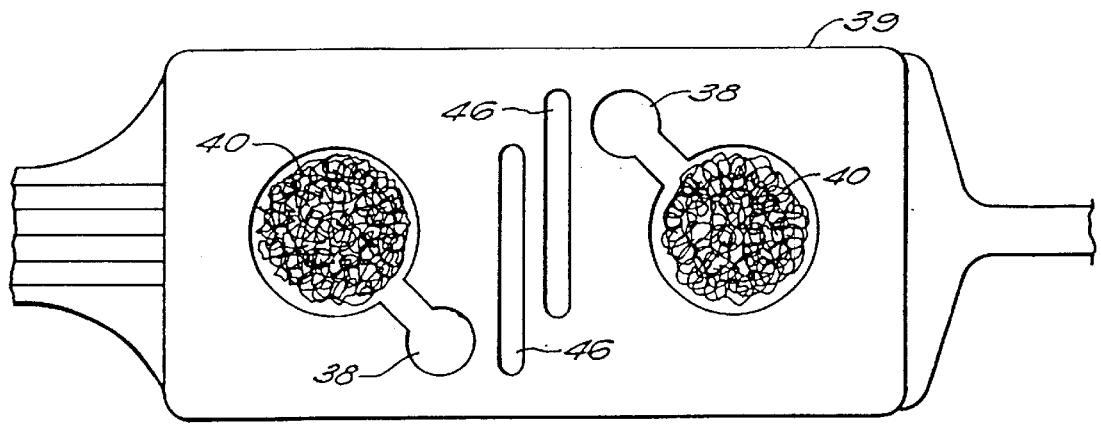
FIG. 12 is a perspective view of the gel blowout pockets and salt bridge barriers utilized by the electrode array shown in FIG. 1.

Referring to FIGS. 4 and 12, the array contains two blowout pockets 38, built into the basepad 39, that allow the gel 40 to adjust its volume over a large area and prevent it from migrating to areas where it could cause malfunction, such as short circuiting the two elements adjacent to one another.

The blowout pockets 38 are formed by cutting cylindrical shapes into the basepad 39 foam material. In addition to the blowout pockets 38, the array 10 also contains two salt bridge barriers 46 which prevent electrolyte gel 40 from one electrode from contacting the gel 40 of the other electrode which could cause the signals to short circuit. The barriers 46 are also cut into the adhesive basepad 39.

In the preferred embodiment a liquid hydrogel is used that rests on the gel pockets 38 cut within the basepad material 39. The gel 40 is retained within the pocket by a polyurethane foam sponge 42. The sponge contains large enough pores that allow the tines 44 to go through the pores and contact the skin 32 during use. The tines 44 then work in the same manner as described in U.S. Pat. No. 5,305,746 the teachings of which are incorporated herein by reference.

Figure 13:
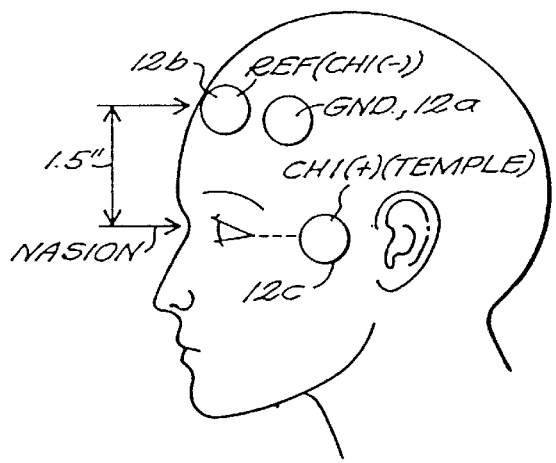
FIGS. 13(a) and 13(b) are representations of a human head showing the locations of the placement of electrodes for one channel monitoring.
Figure 13:
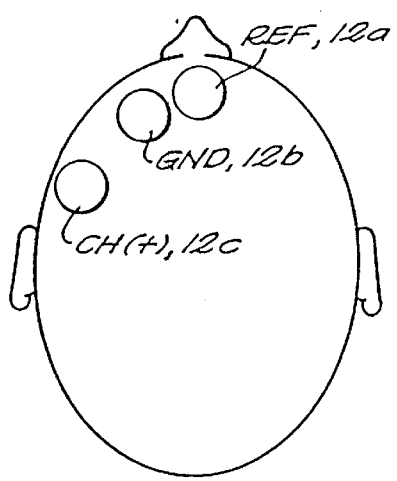

In a number of embodiments, the array 10 is mounted over the forehead with its reference electrode 12b over the center of the forehead. As shown in FIGS. 13(a) and 13(b), the ground electrode 12a is placed over the forehead as well. The third electrode 12c in the satellite body 15 is positioned over the temple area. In most cases, either the right or left temple is acceptable. Such an array may also be used for EMG detection in the facial area.

The tab connector of the present invention is shown in FIGS. 5(a)–5(c). In FIG. 5(a) the conductors 16 which are mounted on a flexible material are inserted into the clip 20 past the edge 46 of the clip 20. The clip 20 includes a hinge 47 which is folded back as shown in FIG. 5(b) until it is rotated a full one hundred eighty degrees as shown in FIG. 5(c). A slot 48 is provided on each side of clip 20 for locking with extension 49 so that the clip 20 stays in a locked and closed position as shown in FIG. 5(c), so that it is ready to be used.

Figure 10:
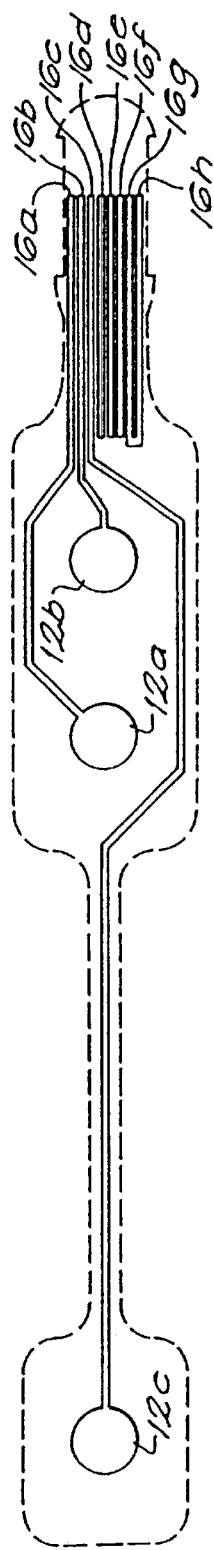
FIG. 10 is a bottom plan view of the electrode array shown in FIG. 1.

Referring to FIG. 10, the tab connector 18 of the array 10 of the preferred embodiment has eight (8) conductors. Out of the eight conductors, three are EEG signal lines 16a, 16b, 16c, and four are logical signal lines 16c, 16f, 16g, 16h used to identify the appropriate array type being connected. In the embodiment shown, the eighth conductor 16d is not used. The unused conductor 16d could be used in other embodiments as an additional EEG signal line or as an additional means to identify an array type. It is important that the sensor sends the identification information to the monitor, so that the monitor can determine the number of active elements used as well as their locations on the head. This way a monitor will auto configure for a particular EEG monitoring session.

Figure 8:
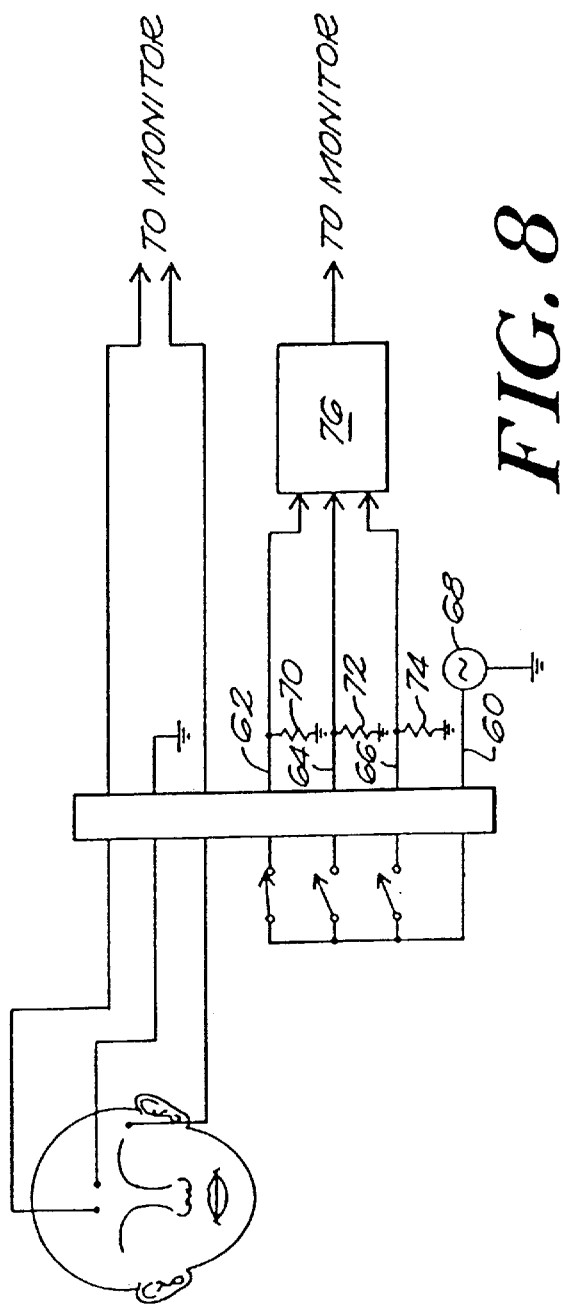
FIG. 8 is a schematic diagram of the configuration coding utilized by the EEG connector system shown in FIGS. 6(a) and 6(b) in its present configuration.

The preferred embodiment uses a three bit binary code identification scheme such as the identification scheme described in U.S. patent application Ser. No. 08/545,981 which is assigned to the assignee of the present invention and the teachings of which are incorporated herein by reference. In such an identification scheme, the code is hard-wired in the flexible circuit of the particular array 10. A digital signal converter in the monitor detects the array ID signals. As shown in FIG. 8, the code is set by selectively shorting a common drive signal line [SEN_DRV] 60 to the three code signal lines [SEN_0:2] 62, 64, 66. These are the three array identification signal lines. The [SEN_DRV] line is pulsed (driven) to a logic high at 8,192 Hz by the pulse generator located on a monitor's digital signal converter. Pulsing the line prevents a fault condition, such as a broken connection, from injecting more than 50 micro amps of current into a patient, as required by medical equipment standards, such as IEC-601-1.

The frequency of the pulse is chosen to be at the Nyquist frequency of the digitizers. These pulses will not interfere with the EEG signal because at this frequency it will alias onto itself only in the first stage of decimation, and will subsequently be filtered out completely by the digital signal processor.

The patient interface connector code signal lines are pulled down to a logic "0" by resistors 70, 72, 74 located in the digital signal converter 146 at the input to the receiver circuit 76, which is a D-Flip-flop in a preferred embodiment. As the common [SEN_DRV] line 60 is driven high by the pulse generator, the patient interface connector code lines [SEN_0:2] 62, 64, 66 are then read (i.e. clocked in) by receiver circuit 76, which transmits the binary code to the monitor 150. The patient interface connector code signal lines that are shorted to the drive signal will be read as a logic "1." The patient interface connector code signal lines that are left open will be read as a logic "0." Such a coding scheme allows for eight different PIC cable types as follows:

| # | Code | Cable Type |
|---|------|------------|
| 1 | 000 | PIC not connected |
| 2 | 001 | 2 channel Bipolar (5 signal wires in use) |
| 3 | 010 | 2 channel Referential (4 signal wires in use) |
| 4 | 011 | 1 channel electrode connection |
| 5 | 100 | 1 channel sensor connection |
| 6, 7, 8 | | Unassigned Spares |

Figure 9:
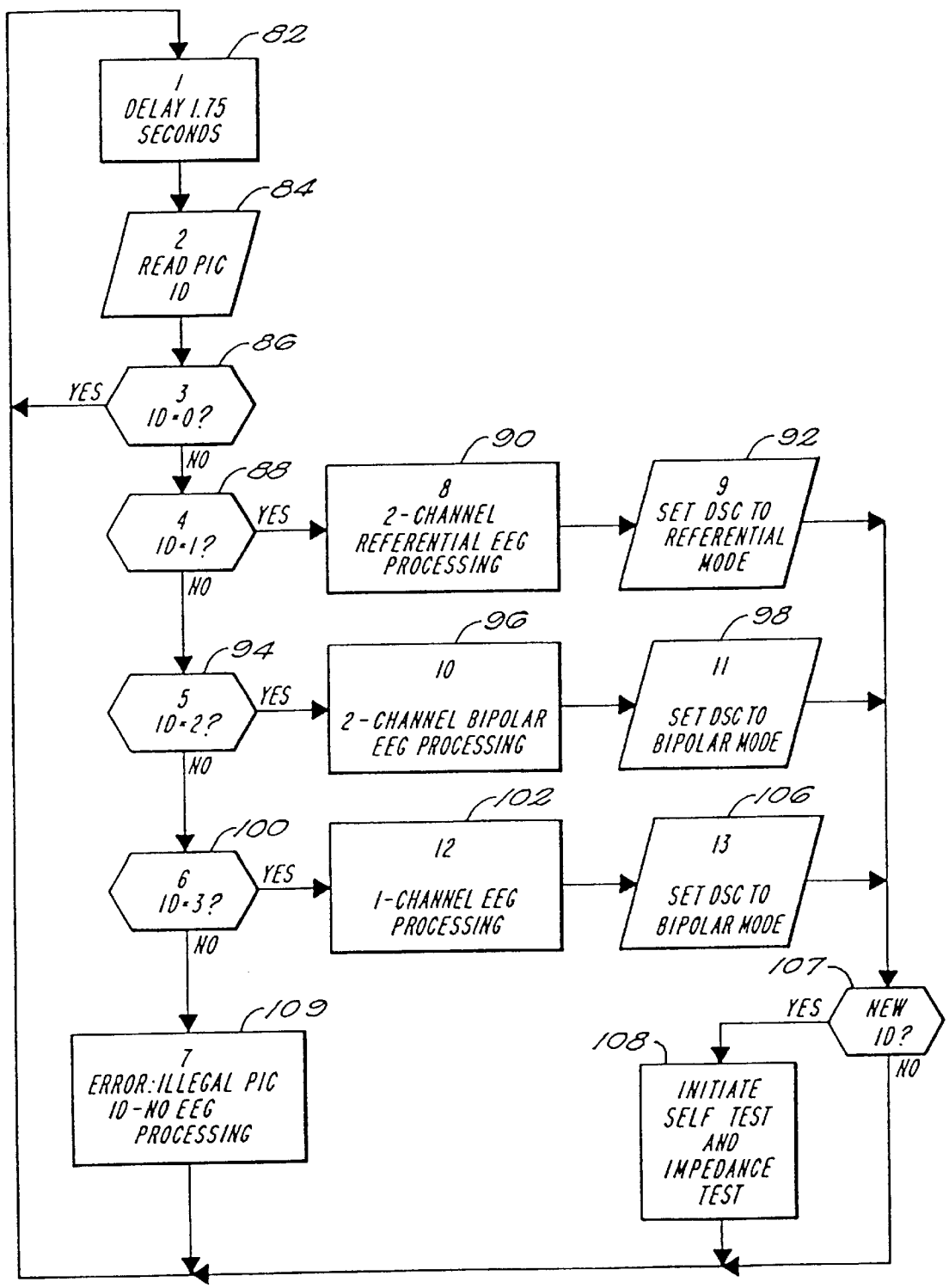
FIG. 9 is a flowchart of the steps taken to identify an electrode array type.
Figure 19:
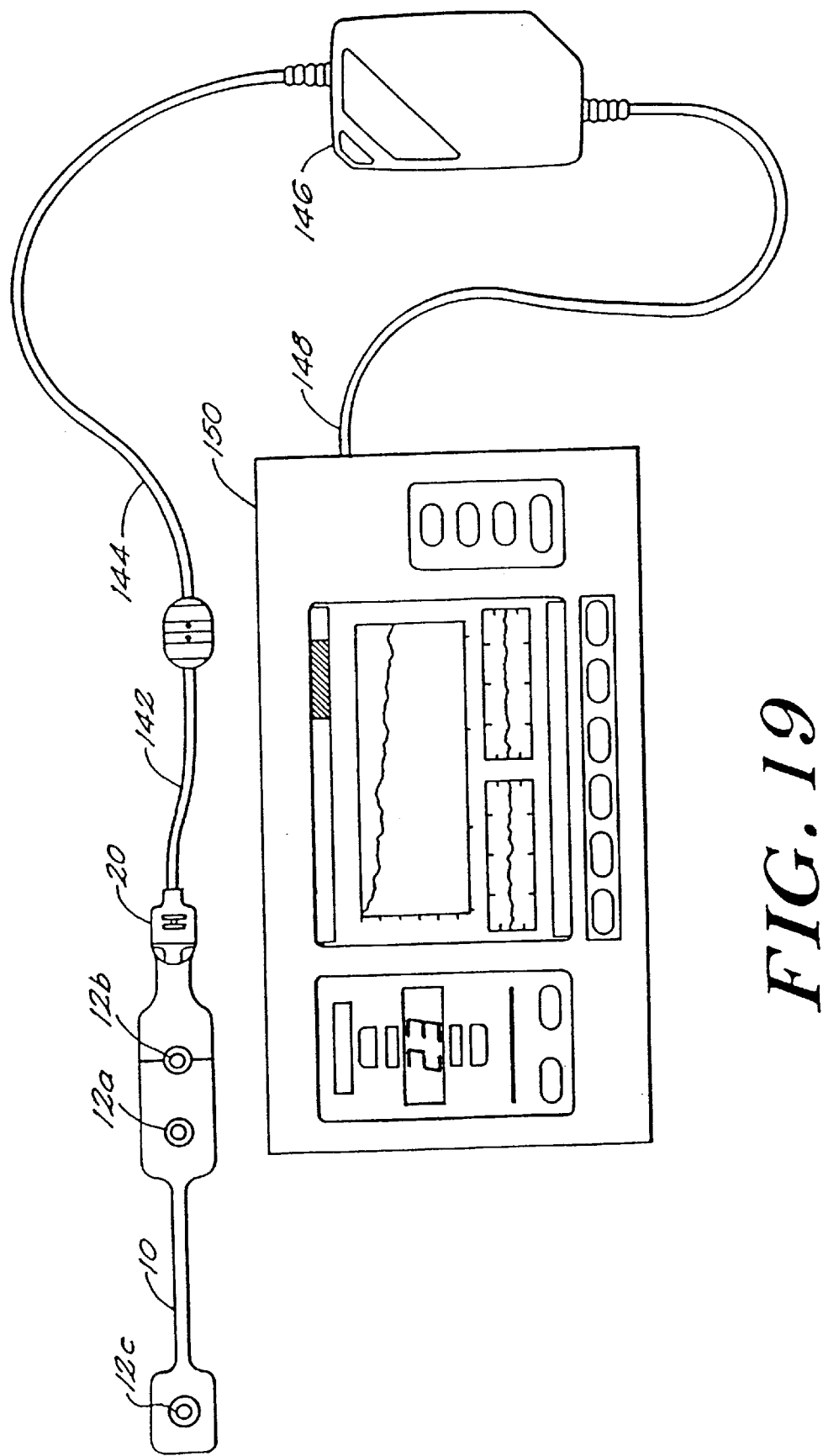
FIG. 19 is a plan view of the components of a system utilizing the electrode array shown in FIG. 1.

Referring now to FIGS. 9 and 19 the process for determining the appropriate PIC will now be described. In step 82, a CPU in the monitor 150 periodically reads the PIC code, which in a preferred embodiment is read every 1.75 seconds. In step 84 the CPU in monitor 150 reads a PIC ID in the manner described above with reference to FIG. 8. If the PIC ID is determined in step 86 to be "000," (which indicates that a PIC is not connected) the system reiterates the process after each 1.75 second delay and continues to attempt to read a new PIC ID.

If the PIC ID is determined in step 88 to be "010," a two channel referential EEG electrode set is detected and the monitor 150 is configured for 2-channel referential EEG processing in step 90. The digital signal convertor is set to referential mode in step 92. If, in step 94, the PIC ID is equal to "010," the system recognizes a two channel bipolar EEG electrode set and the monitor 150 is configured for the appropriate EEG processing in step 96. The digital signal convertor 146 is then set in step 98 to bipolar mode.

If the PIC ID is determined in step 100 to be equal to "011," the system has detected a one channel EEG processing cable and the monitor 150 is configured for 1-channel EEG processing in step 102. In step 106, digital signal converter is set to bipolar mode. If any other PIC ID is detected, error messages are generated and displayed in step 107 indicating that an illegal PIC ID was detected, and that no EEG processing should occur. After the CPU in monitor 150 determines that the PIC ID is valid, the monitor checks if the PIC ID is a new PIC ID. If a new PIC ID is recognized the monitor initiates a self test in step 108 followed by an electrode impedance test in step 109. After this series of steps the system again returns after a 1.75 second delay to read additional PIC IDs in step 82.

In alternate embodiments where four pins are allocated for PIC IDs, the digital signal convertor 146 can recognize up to 15 different combinations of pigtail, PIC or connector type.

The current connector system allows either a single channel electrode array or a dual channel electrode array. As shown in FIGS. 7(a)–7(e), it also provides a keying safeguard that allows for the connector to be selective as to what can physically be plugged into it. By modifying the height of the connector rails 50 one can allow for a specific array to be a master key (FIG. 7(a)) and other arrays to be specific to a mating connector. This keying mechanism can be used for example to physically differentiate between array types. For instance, an array that allows single and dual channel monitoring, and one that allows only dual channel monitoring. The master key is then available to connect to all monitors indiscriminately. For instance, it can be used to insert a test circuit to service the monitor, or used to insert a multipurpose array.

Figure 6A:
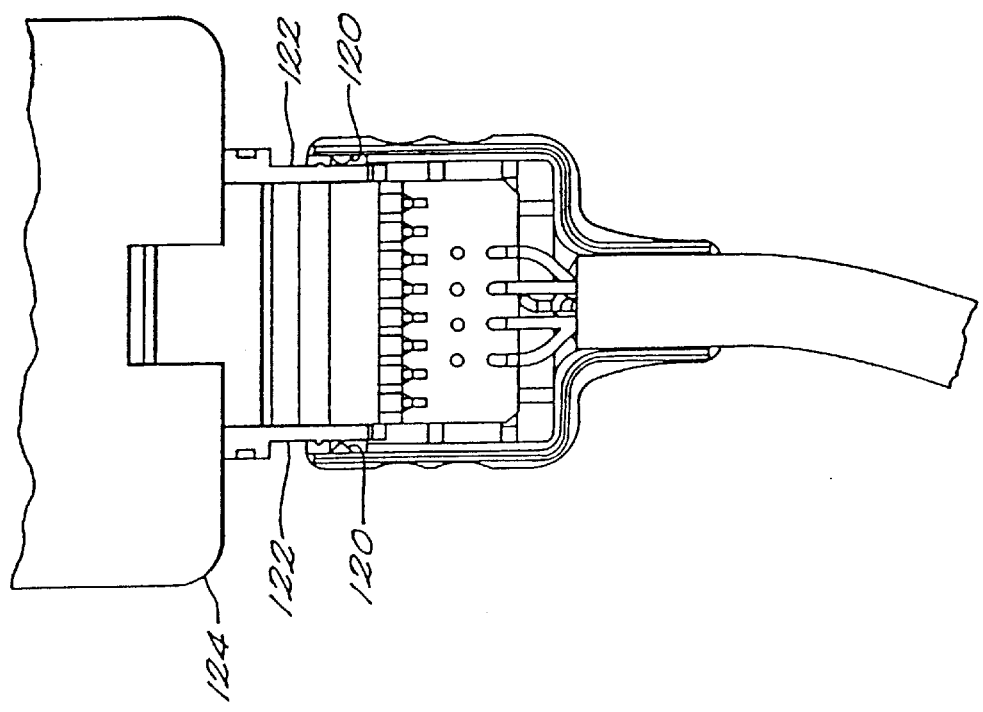
FIGS. 6(a) and 6(b) are top plan views of the EEG connector system used with the electrode array shown in FIG. 1 with FIG. 6(a) showing the connectors engaged and FIG. 6(b) showing the connectors disengaged.
Figure 6B:
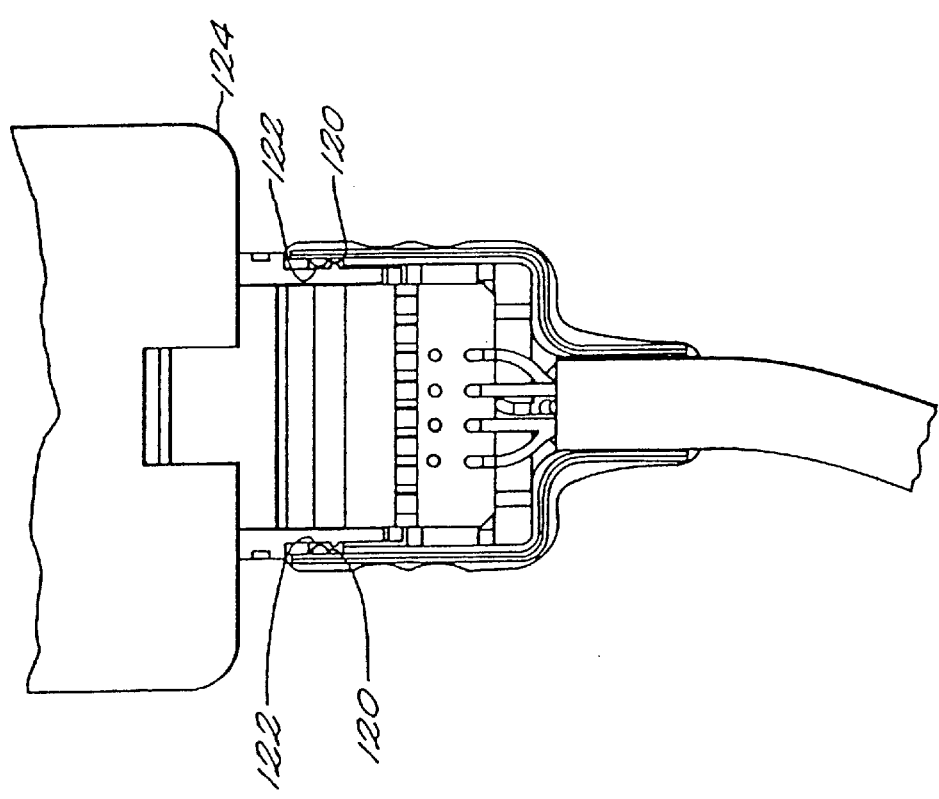
Figure 7A:
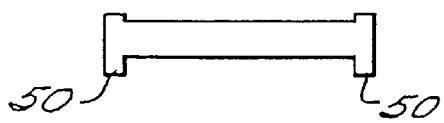
FIGS. 7(a) through 7(e) are elevational views of keys used in the EEG connector system shown in FIGS. 6(a) and 6(b)
Figure 7B:
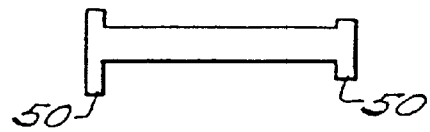
Figure 7C:
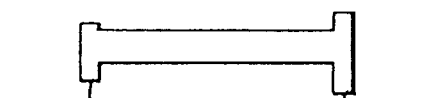
Figure 7D:
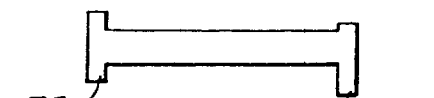
Figure 7E:
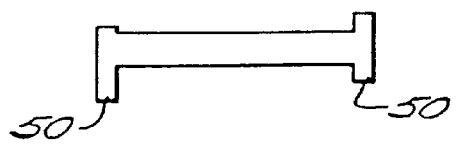

Referring to FIGS. 6(a) and 6(b), the tab connection on the array has a locking mechanism, including extension 120 and receptor region 122 that secures it to the reusable connector 124. The locking action provides the user with tactile and audible feedback.

The reusable connector 124 includes a printed circuit board with contacts and wires from a cable attached to it. The printed circuit board is then inserted into an assembly of two pre-molded housings secured together by ultrasonic welding.

The electrode array 10 described above is used in connection with a new non-standard electrode positioning (montage) for measuring the effects of anesthetics on the brain as well as other cerebral phenomena.

Referring to FIGS. 13(a) and 13(b), one embodiment of this montage is shown in which the reference electrode 12 is placed in the center of the forehead with the satellite electrode 12 being placed on the temple at eye level above the ear. This montage has several advantages over previously described montages, as it makes it easy to locate the electrodes on the patient, the electrodes are easy to apply to the patient and the EEG signal and the amplitude of such signal are sufficient for the purposes for which they are used.

The location of the electrodes is important for monitoring the effects of anesthetics. Prior art for monitoring the effects of anesthetics have described EEG systems using from 2 to 19 EEG channels, where the electrode locations have been identified by the international 10–20 systems. The electrode arrays described above use 1 or 2 EEG channels. The specific electrode locations described in this patent are positioned in a unique anterior area of the subject's head from which EEG signals have not traditionally been taken. These anterior placed arrays take advantage of the global nature of the effects of anesthetics on the brain. That is to say that the global effects of anesthetics are reflected in the EEG detected near the anterior cerebral cortex. The electrode array described above provides a rather large EEG signal because of the inter-electrode spacing that has been selected. The electrodes, however, are not so widely spaced as to increase a noise signal generated by the subject (e.g. EKG). In any signal processing system, increases in signal amplitude without an increase in the noise amplitude is desirable. This is particularly true with EEG monitoring because EEG is on the order of one hundred times smaller than the electrocardiogram (EKG). The electrode array 10 facilitates the locating of the electrodes 12 at positions referenced to easily identified anatomical landmarks (i.e. center of the forehead, eye socket). In addition, the electrode locations are entirely out of the subject's hair. This allows for easy application of the electrodes without the need to shave or otherwise part the subject's hair.

A system utilizing the electrode array of the present invention may be configured in one or two channel monitoring modes. For the two channel mode shown in FIGS. 15(a) and 15(b), one EEG channel measures from an electrode location on the subject's forehead to the left of the lower temple area, proximal to the left eye socket (malar bone). The second EEG channel measures from the same forehead electrode to the right lower temple area, proximal to the eye socket. A non-measurement ground electrode is also placed on the patient's forehead. The two channel system has the advantages of signal redundancy (two channels of signal instead of one channel) and improved signal to noise ratio. The one channel configuration, an example of which is shown in FIG. 1, uses the center forehead electrode plus either the left or right electrode described above plus the ground electrode. The one channel configuration has the advantage of using less space on the subject's head thereby making an operation on the head easier since there is a greater area over which to maneuver. The one channel configuration being easier to apply because of the use of one less electrode.

Figure 11:
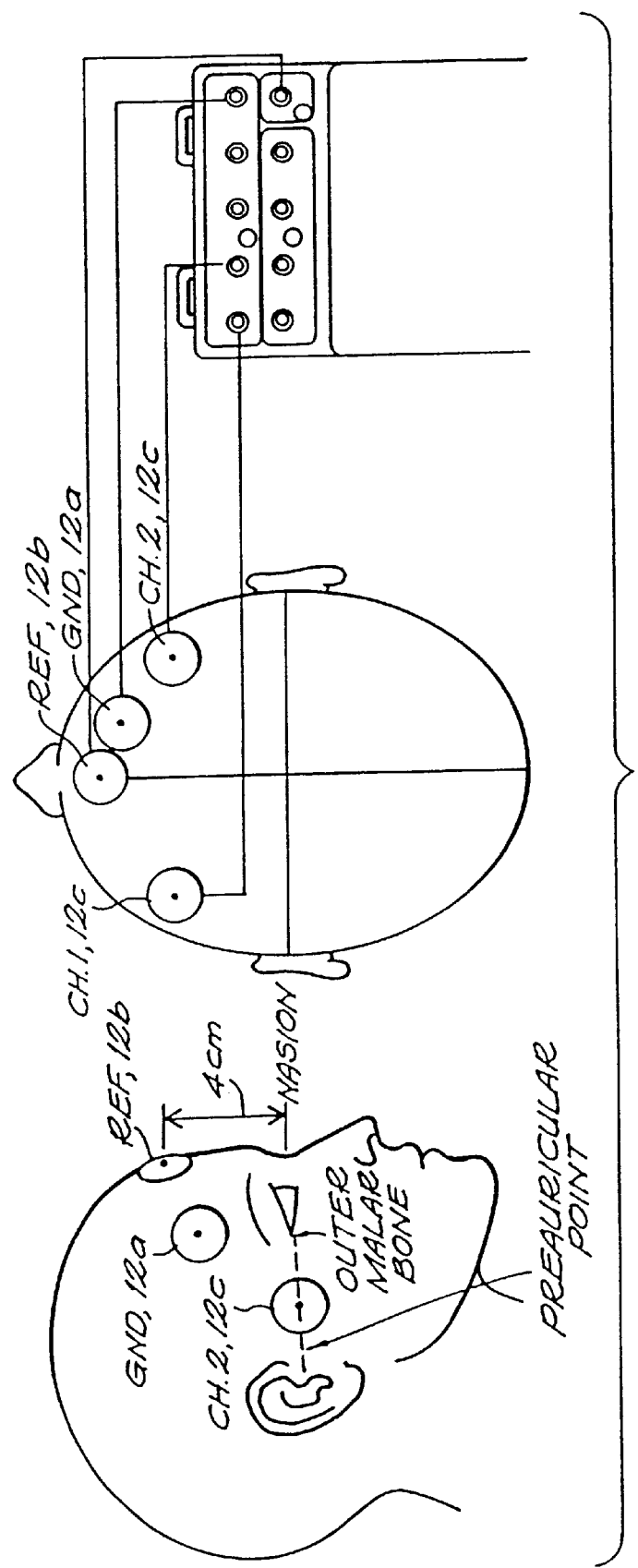
FIG. 11 is a diagram showing locations on the head where electrodes are positioned for 2 channel monitoring.
Figure 15A:
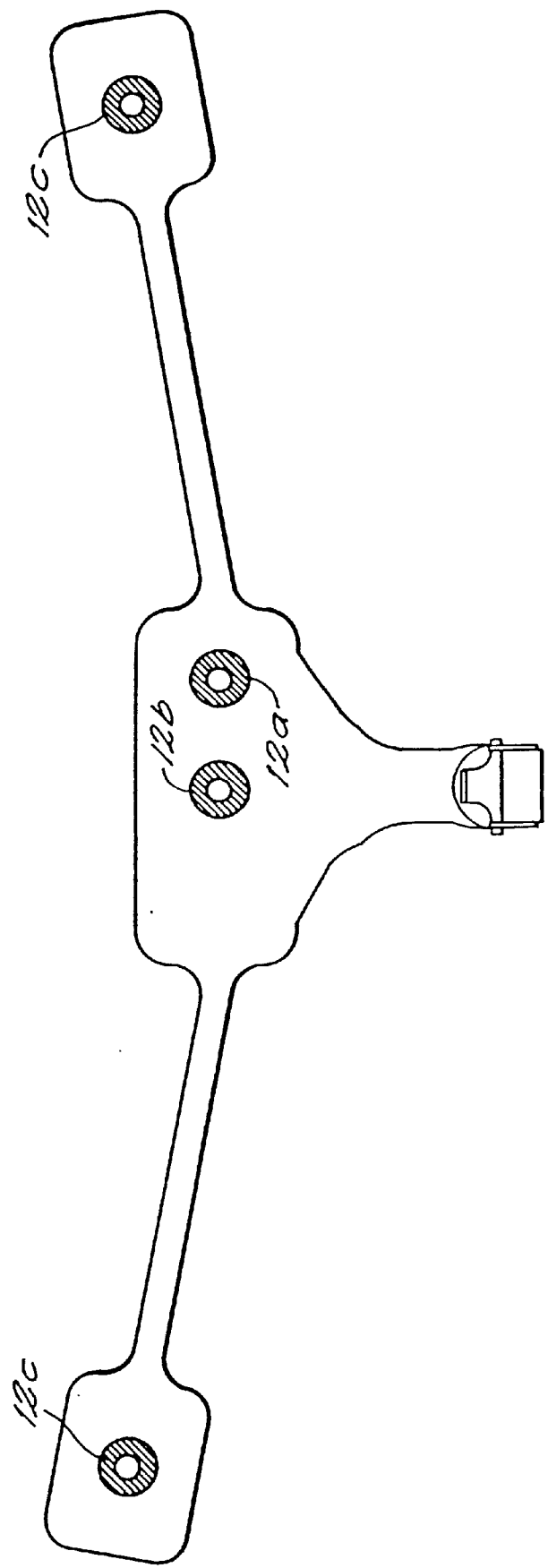
FIG. 15(a) is a top plan view of an alternate embodiment the electrode array of the present invention which includes two elements for temple connection.
Figure 15B:
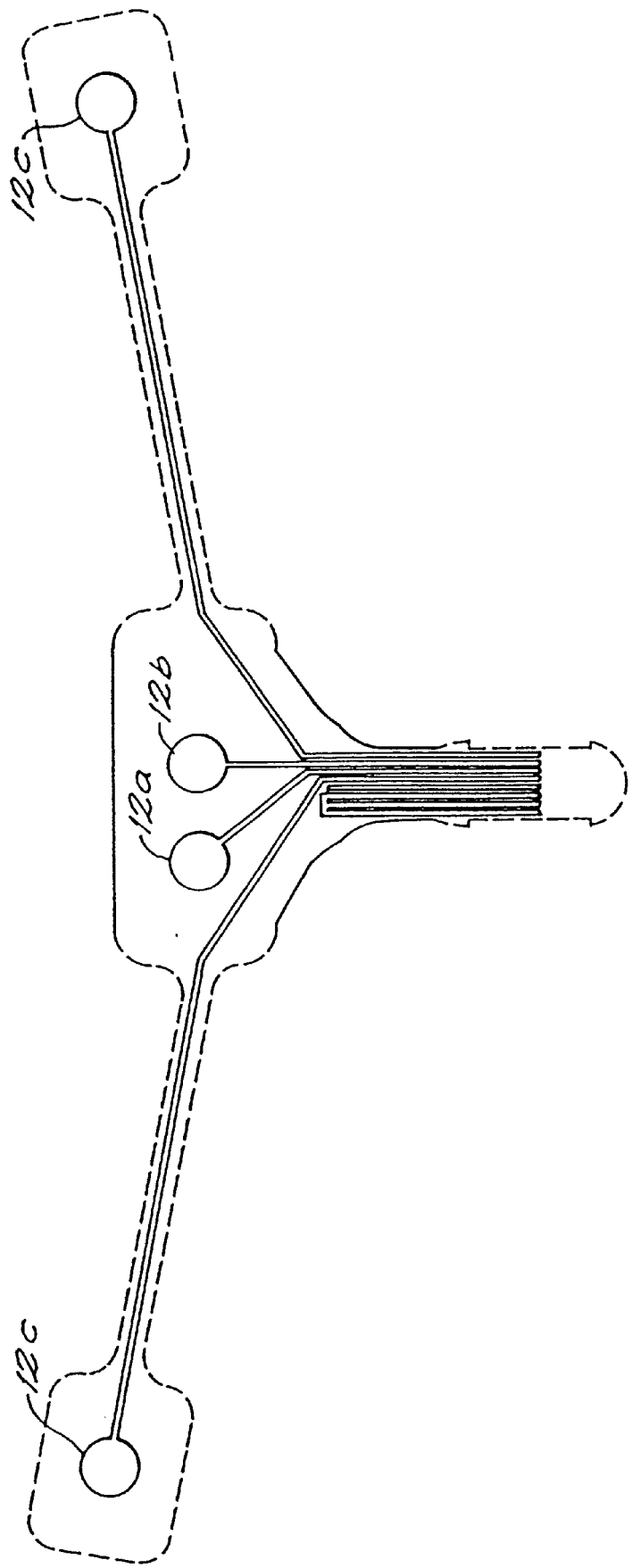
FIG. 15(b) is a bottom plan view of the electrode array shown in FIG. 15(a)

Referring to FIGS. 15(a) and 15(b), an alternate embodiment of the present invention is shown in which the array 10 of electrodes 12 includes two temple electrodes 12c that allow for depth of anesthesia, burst suppression, ischemia monitor, and EEG recordings as well as EMG detection. When a two channel system is used, the signals could be averaged together or the second channel could be used as a backup signal if the first channel signals are lost. The placement of the electrodes on a human head in such a two channel system is shown in FIG. 11. Referring to FIG. 10, in this configuration, conductor 16d is used to provide the signal from the second temple.

Figure 16:
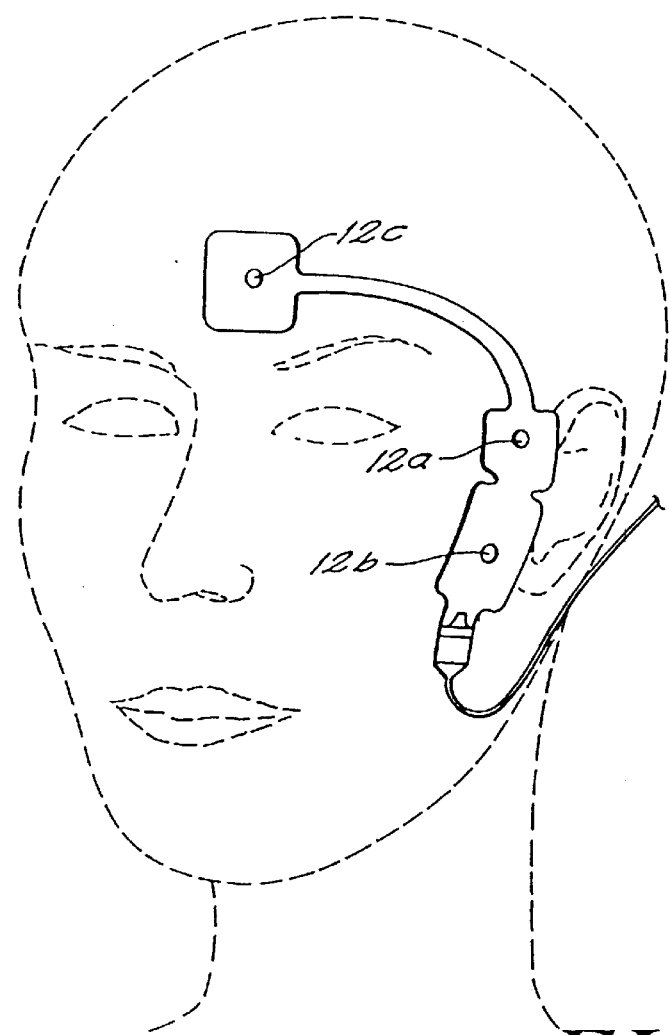
FIG. 16 is a representation of a human head with an alternate embodiment of the electrode array locating the connector in an alternate location, being placed thereon.

Referring to FIG. 16, the same array 10 described above in connection with FIG. 1 is used in a different manner with the center of the main body 14 of the array 10 being placed over the temples and the electrode 12c on the satellite body 15 becomes the reference electrode. This configuration offers the advantage of keeping the cable away from the face of the patient.

Figure 17:
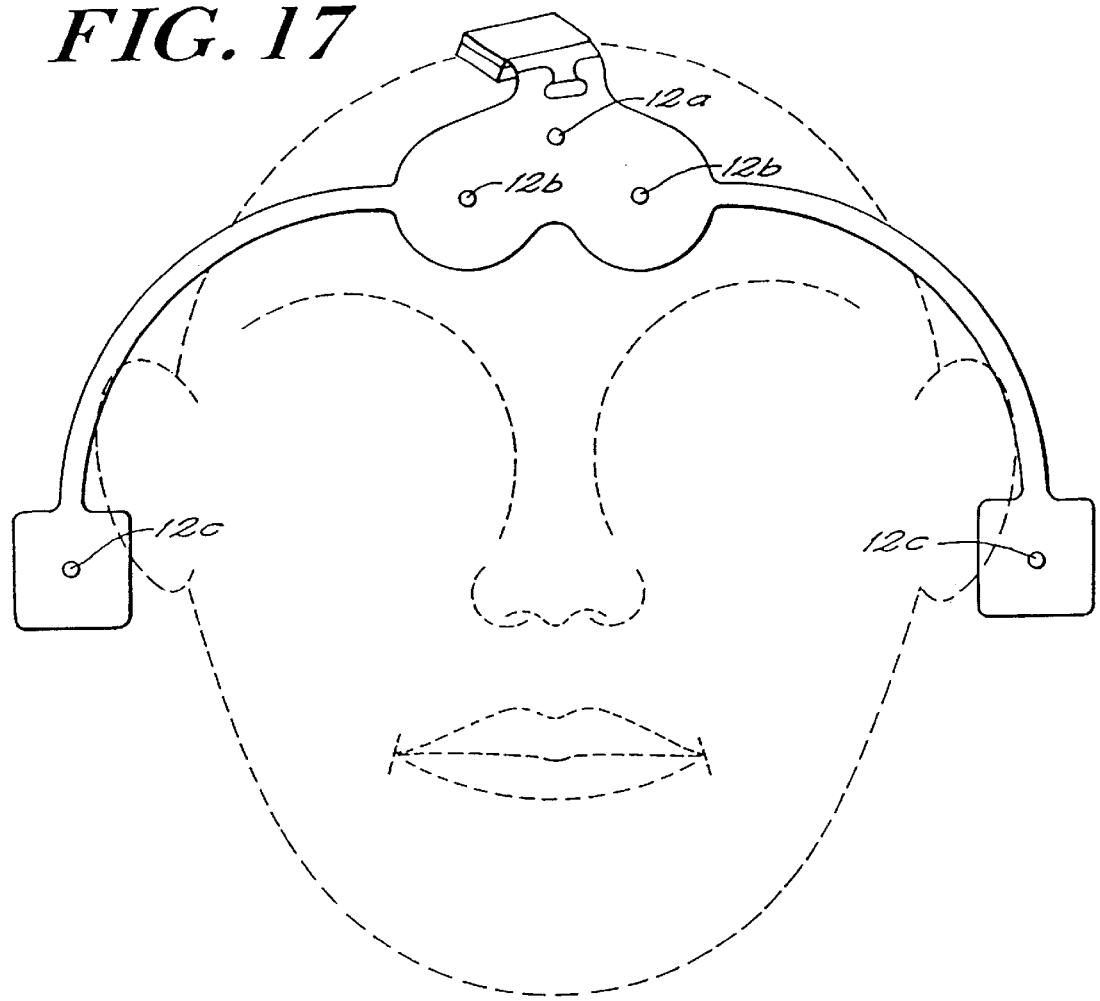
FIG. 17 is another representation of a human head on which another alternate embodiment of the electrode array of the present invention is positioned; using the mastoid locations to place the two satellite electrodes.

As shown in FIG. 17, another array 10 of electrodes 12 is shown with a ground connection 12a two frontal connections and two mastoid connections that can be used for depth of anesthesia, burst suppression, ischemia monitoring, and EEG recordings as well as EMG detection. As with the embodiments shown in FIGS. 15(a) and 15(b), the configuration shown in FIG. 17 can be used to capture a hemisphere signal on each side of the head in order to produce bipolar readings.

In alternate embodiments, an array of electrodes will contain other passive devices such as but not limited to resistors, capacitors, or jumpers, for purposes of generating a code for self configuration.

Figure 18:
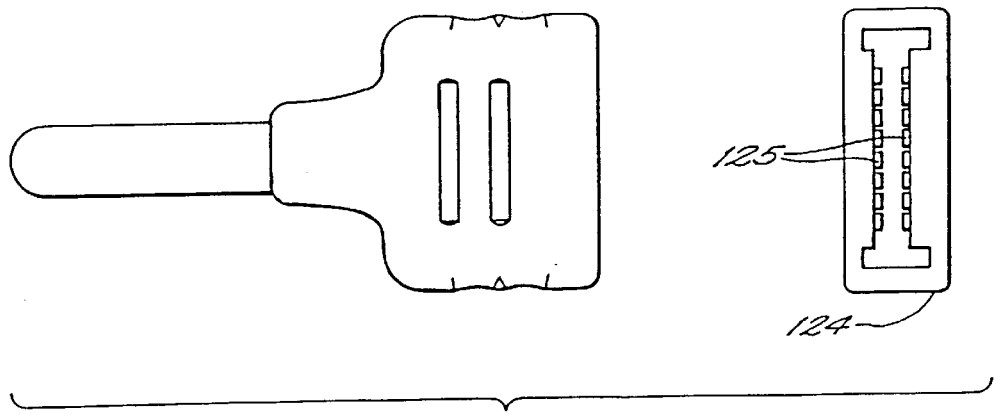
FIG. 18 is a side plan view of a female portion of an alternate embodiment of the connector used in the present invention and a top plan view of the connector.

In another embodiment shown in FIG. 18, the array 10 of multiple electrodes 12 comprises of a flexible circuit with conductors that terminate on a tab connection that is double sided. The mating connector 124 has contacts 125 on top and bottom. This allows an increase in the density of the circuit while keeping the size of the connector to a small profile. It also allows for the separation of signals that are of digital nature from those of physioelectric nature. This reduces the amount of noise on the EEG signals.

Referring now to FIG. 19, the electrode array 10 is shown in use with an EEG monitor. The electrode array 10 is connected through connector 20 to a patient interface cable 142 which in turn is connected to a pigtail cable 144. The pigtail cable 144 is connected to a digital signal converter 146 which in turn is connected to monitor 150 through monitor interface cable 148. In another embodiment, the digital signal converter may be embedded in the monitor thereby eliminating the need for cables 144, 148 or the electrode array 10 could also be connected to cable 144 thereby eliminating the need for cable 142.

While the foregoing invention has been described with reference to its preferred embodiments, various alterations and modifications will occur to those skilled in the art. All such alterations and modifications are intended to fall within the scope of the appended claims.

What is claimed is:

1. An array of electrodes, including only four electrodes, for monitoring physiological electrical signals, said array comprising:

a flexible body having a main portion, two satellite portions and a flexible connector connected between said main portion and each of said two satellite portions;

two electrodes of the four electrodes being positioned on said main portion and one electrode of the four electrodes being positioned on each of said two satellite portions.

2. The array of electrodes for monitoring physiological electrical signals of claim 1 wherein conductors are positioned on said flexible body to carry signals from said electrodes.

3. The array of electrodes for monitoring physiological electrical signals of claim 2 wherein said array further comprises a tab connection into which said conductors are inserted and locked.

4. The array of electrodes for monitoring physiological electrical signals of claim 3 wherein said tab connection comprises a body into which said conductors are inserted, said body having a first end and a second end;

a hinge position between said first end and said second end about which said second end is rotated to be positioned in close proximity to said first end;

a locking mechanism for locking said second end adjacent said first end.

5. The array of electrodes for monitoring physiological electrical signals of claim 3 wherein said tab connector further comprises at least two rails for guiding said connector into a reusable connector of a monitor, said rails being dimensioned uniquely for a particular application.

6. The array of electrodes for monitoring physiological electrical signals of claim 2 wherein said conductors for said array are Ag/AgCl conductors.

7. The array of electrodes for monitoring physiological electrical signals of claim 1 wherein said array further comprises an adhesive material on one surface of said flexible body.

8. The array of electrodes for monitoring physiological electrical signals of claim 1 further comprising non-conductive tines positioned beneath each electrode for separating layers of a patient's skin.

9. The array of electrodes for monitoring physiological electrical signals of claim 1 further comprising electrolytic gel and a blow-out compartment mounted on each electrode for storing said electrolytic gel out of contact with gel from any other electrode.

10. The array of electrodes for monitoring physiological electrical signals of claim 8 further comprising a sponge mounted on each electrode through which said tines pass to contact a patient's skin.

11. The array of electrodes for monitoring physiological electrical signals of claim 1 further comprising a salt bridge barrier for preventing electrolytic gel in contact with one of said electrodes from contacting electrolytic gel in contact with a second of said electrodes.

12. The array of electrodes for monitoring physiological electrical signals of claim 1 further comprising a connector attached to said flexible body and means for storing a code unique to the array in said connector attached to said flexible body.

* * * * *